United States Patent [19]

Straihammer

[11] 4,276,025

[45] Jun. 30, 1981

[54] DENTAL HANDPIECE

[75] Inventor: Reinhard Straihammer, Einhausen, Fed. Rep. of Germany

[73] Assignee: Siemens Aktiengesellschaft, Berlin & Munich, Fed. Rep. of Germany

[21] Appl. No.: 100,145

[22] Filed: Dec. 4, 1979

[30] Foreign Application Priority Data

Dec. 22, 1978 [DE] Fed. Rep. of Germany ....... 2855796

[51] Int. Cl.³ .......................... A61C 1/12; A61C 1/08
[52] U.S. Cl. ..................................... 433/105; 433/133
[58] Field of Search ............... 433/105, 130, 126, 133, 433/146; 408/133; 74/416, 417, 332, 812

[56] References Cited

U.S. PATENT DOCUMENTS

| 3,092,908 | 6/1963 | Flatland | 433/92 |
| 3,229,369 | 1/1966 | Hoffmeister et al. | 433/133 |
| 4,047,301 | 9/1977 | Eibofner | 433/120 |

FOREIGN PATENT DOCUMENTS

| 283565 | 1/1914 | Fed. Rep. of Germany | 433/130 |
| 890118 | 9/1953 | Fed. Rep. of Germany | 433/130 |

*Primary Examiner*—Gene Mancene
*Assistant Examiner*—John J. Wilson
*Attorney, Agent, or Firm*—Hill, Van Santen, Steadman, Chiara & Simpson

[57] ABSTRACT

In a dental handpiece having a drive motor, a grip section coupled to the drive motor and terminating in a head part having a socket for supporting a tool for rotation, the grip section having a drive train for transmitting rotation motion of the drive motor to the socket with the drive train including at least two drive shaft sections interconnected by meshing gears and the grip section having an angle portion so that one drive shaft section adjacent the socket extends at an angle of inclination to the other drive shaft section on the axis of the drive motor characterized by an improvement of the angle of inclination being formed in at least two stages with an additional drive shaft section interposed between the one drive shaft section adjacent the socket and other drive shaft section on the axis of the drive motor. The additional drive shaft section will form an individual angle with each of the two drive shaft sections with each individual angle being less than the angle of inclination but at least one-fourth of the angle of inclination and preferably being approximately half of the angle of inclination.

4 Claims, 2 Drawing Figures

DENTAL HANDPIECE

BACKGROUND OF THE INVENTION

The present invention is directed to a dental handpiece with a drive motor having a grip section or handpiece part coupled to the drive motor and supporting a head part at one end with a socket for mounting a tool for rotational movement. The grip section includes a drive train for transferring the rotary motion of the motor to the socket and the drive train includes at least two drive shaft sections interconnected by meshing gears and inclined with respect to one another at an angle of inclination.

Dental handpieces, which have an angle portion and are called angled handpieces, are known and have two handpiece parts usually arranged to be inclined to one another at an angle of approximately 15°–21° and as a rule at an angle of 20°. The angle of inclination is particularly selected for reasons of operating technology such as to provide the tip of the tool rotatably seated in a socket of the head portion to lie approximately on an extension of the axis of handpiece part which contains the drive motor. The gear train having gears for either stepping up or respectively stepping down the RPM's from the drive motor to the tool is arranged in the grip section and particularly in the location of the angle portion. In order to be able to achieve the required transmission ratios for example a step up ratio of 1:3 or a step down ratio of 3:1, it is necessary in the known dental handpiece to provide gear wheels which are relatively large in diameter at the location of the angled portion to the handpiece or grip section. In such an arrangement, it is extremely difficult to incorporate cooling agent lines, which have a sufficiently large cross section and to include the necessary coupling and sealing portion particularly in the angle portion area which is usually a separation point for the two handpiece parts forming the grip section. These problems of including all of the necessary parts are particularly difficult when it is desired to maintain the total diameter of the handpiece as small as possible.

SUMMARY OF THE INVENTION

The present invention is directed to providing a dental handpiece, which has an angled portion in the grip section and has a diameter, which in comparison to known constructions is kept as small as possible but provides room for cooling lines with the sufficient cross sectional size and room for sealing means at the various separation points.

To accomplish these tasks, the present invention is directed to an improvement in a dental handpiece having a drive motor, a grip section coupled to the drive motor and terminating in a head part having a socket for supporting a tool for rotation, said grip section having drive train means for transmitting rotational movement of the drive motor to the socket, said drive train means including at least two drive shaft sections interconnected by meshing gears, said grip section having an angled portion so that one drive shaft section adjacent the socket extends at an angle of inclination to the other drive shaft section on the axis of the drive motor. The improvements are that the angle of inclination is formed in at least two stages with an additional drive shaft section interposed between the one drive shaft section adjacent the socket and the other drive shaft section on the axis of the drive motor, said additional drive shaft section forming an individual angle with each of the two drive shaft sections with each individual angle being less than the angle of inclination.

The improvement, which provides an additional drive shaft section, enable providing a dental handpiece utilizing smaller driving gear in the drive train and therefore enables providing the dental handpiece having a reduced exterior diameter but retaining substantially the same overall length. The incorporation and laying out of the cooling agent lines within the handpiece is easier in view of the improvement of obtaining the angle of inclination in stages. The improvement also enables increasing the cross sectional dimension of the cooling agent line which reduces the dangers of calcification and/or blockage. A further advantage is that the abrupt and sharp bend, which is present in the known dental handpieces, has been eliminated and replaced by a soft transition from the straight to the inclined handpiece part.

DESCRIPTION OF THE PREFERRED EMBODIMENTS

Figure 1:
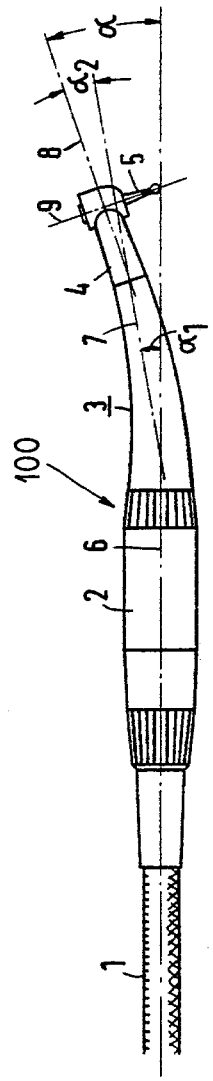
FIG. 1 is a side elevational view of a dental handpiece in accordance with the present invention having a drive motor part, an angled handpiece part and head part.

The principles of the present invention are particularly useful in a dental handpiece generally indicated at 100 in FIG. 1. The dental handpiece 100 is composed of a drive motor section or part 2, which is connected to a supply hose 1, which extends to a source for electrical current for the motor and sources of cooling fluid whose use will be discussed hereinafter. A handpiece part or grip section 3 is connected to the drive motor or part 2 and extends to a head part 4 which has a housing rotatably supporting a tool 5. For transmitting the rotary motion from the drive motor in the drive motor part 2 to the tool 5, the handpiece contains a drive train means including a plurality of drive shaft sections which are engaged with one another and whose axes are provided with the reference symbols 6, 7, 8 and 9.

The angle of inclination $\alpha$, which is the angle between the axis 8 for the head part 4 and the axis 6 for the drive motor part 2, for a number of reasons according to operating technology generally lies between 18° to 21° so that the tip of tool 5 is on an extension of axis 6. As illustrated, the angle of inclination $\alpha$ is formed in stages by angle $\alpha_1$ and $\alpha_2$ in the grip section, wherein $\alpha_1$ is determined by the point of intersection of the two axes 6 and 7 and $\alpha_2$ is determined by the point of intersection of the axes 7 and 8. The two angles $\alpha_1$ and $\alpha_2$ are dimensioned in such a manner that upon consideration of the necessary gear step-up or step-down of the module or respectively, the number of teeth of the gears required for reasons of stability, a harmonic, external contour with a continuously decreasing exterior diameter from the one end to the other end of the handpiece can be achieved without increasing the length of the handpiece. It is expedient if both angles $\alpha_1$ and $\alpha_2$ are greater than one-fourth the total angle $\alpha$. Preferably, the angles of $\alpha_1$ and $\alpha_2$ are approximately half of the total angle $\alpha$ and have a range of approximately 8° to 12°.

Figure 2:
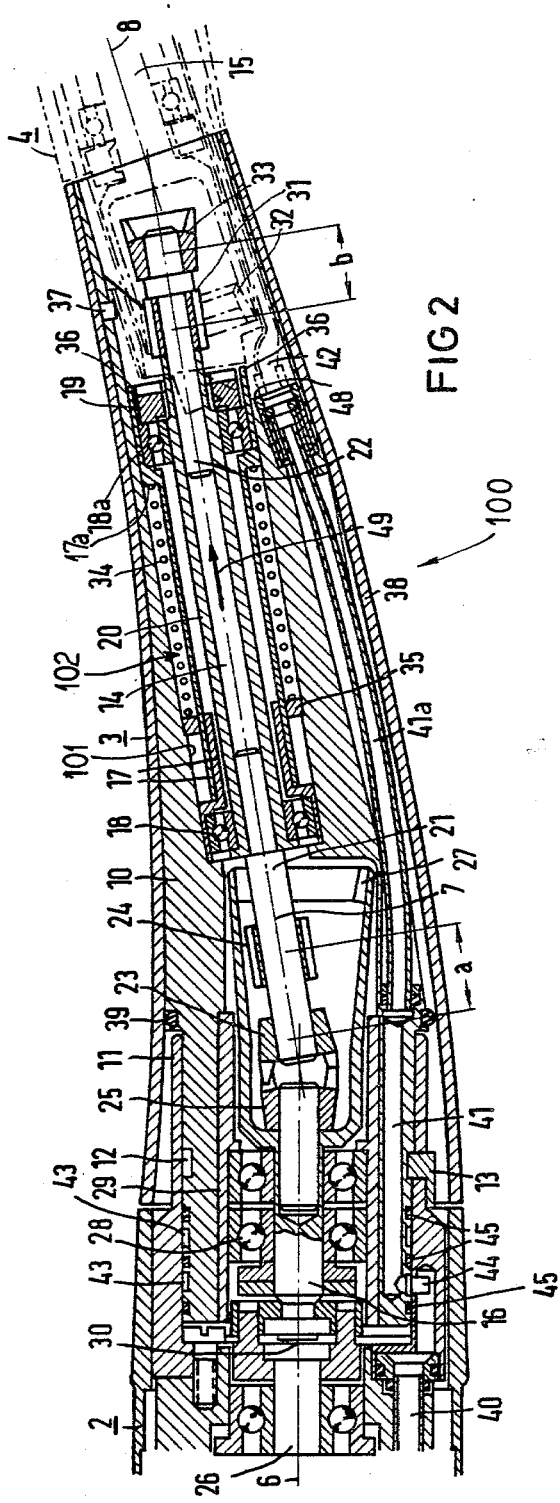
FIG. 2 is a longitudinal cross sectional view of a portion of the dental handpiece of FIG. 1.

In FIG. 2, the handpiece part or grip section 3 along with part of the motor drive part 2 are illustrated and the head part 4 is shown in chain lines. The handpiece part 3 contains a basic body member or portion 10. As illustrated, the part or portion 10 is connected to the motor part 2 by being telescopically received in a guide bushing or sleeve 11 of the part 2 so that the grip section 3 and member 10 have a rotatable connection with the drive motor part 2. The guide bushing or sleeve 11 extends concentric to the drive shaft axis 6 of which the drive shaft 26 of the motor lies and which axis 6 is the axis of symmetry for the motor part 2. As illustrated, the member 10 is rotatably received in the guide sleeve 11 but is held from axial displacement by a stop bolt 13 of the known construction which is received in the annular groove 12 of the member 10.

The member 10 supports a first drive shaft section 16 for rotation on an axis 6 and supports a second or additional drive shaft section 14 to rotate on an axis 7. The head part 4 supports a third drive shaft section 15 to rotate on the axis 8. The drive shaft section 14 is formed by a tubular member 20, which receives solid shaft portions 21 and 22 at each end. To mount the shaft portion 14 in a bore 101 in the member 10, mounting means, which are generally indicated at 102, include a hollow sleeve member 17 which is formed by a pair of sleeves that are secured together. The sleeve member 17 supports races of ball bearings 18 and 18a which bearings rotatably support the tubular sleeve 20 of the second shaft section 14. As illustrated, the right hand end of the sleeve member 17, which terminates in an end surface 36, receives a slotted ring 19 to secure one of the bearings 18a therein.

The shaft 21, which is pressed into the end of the tubular member 20, supports a first gear 23 and a second gear 24 with the first gear 23 being a crown gear disposed at the end and axially displaced a distance a from the second gear 24 which is a spur gear. As illustrated in FIG. 2, the crown gear 23 is engagement with a crown gear 25 of the first shaft section 16 and both crown gears 23 and 25 have the same number of teeth so that the RPM's of the shaft 26 of the drive motor 2 are directly transmitted to the drive shaft section 14 via the drive shaft section 16 and therefore a ratio of 1:1 is provided. The drive shaft section 16 also has a coaxial second gear 27, which is axially spaced from the first gear 25 and the gear 27 has teeth on an inside surface of a cup-shaped member which teeth extend towards the axis of the drive shaft. The teeth of the gear 27 will engage with the spur gear 24 when the drive shaft section 14 has been displaced in the direction of arrow 49 by an amount to enable engagement of the second gear 24 of the section 14 with the second gear 27 and disengagement of the crown gears 23 and 25 which are the first gears of each of the shaft sections. Since the gear 27 has approximately 2.5 times the number of teeth of the gear 24, the shaft section 14 will be driven at a step up ratio of 1:2.5 when the gears 24 and 27 are engaged.

As illustrated, the first drive shaft section 16 is releasably coupled by a coupling device 30 to the drive shaft 26 of the drive motor. The shaft 16 is supported for rotation by bearings 28 in a sleeve or bushing 29 which is received in a bore in the member 10.

At the other end of the drive section 14, the shaft 22 is provided with two axially spaced gears including a spur gear 31 and a crown gear 33. As illustrated, the spur gear 31 will engage with a gear 32 on the shaft section 15, which gear 32 has a structure similar to the gear 27 on the shaft section 16. The gear 33 is illustrated as a crown and is pressed on the pen-like shaft 22 at an axial distance b from the gear 31. In the position illustrated, the crown gear 33 is disengaged from any gear part of the drive shaft section 15.

The means for mounting enables axial displacement of one of the shaft sections such as the second shaft section 14 from a first position with the crown gears 23 and 25 in engagement to a second position with the spur gear 24 engagement with the gear 27. The means 102 accomplishes this by the sleeve member 17 being slideably received in the bore 101 and having a biasing means such as the spring 34 acting between a ring shaped stop 35 and a shoulder 17a to urge displacement of the sleeve 17 and the shaft 14 in the direction of arrow 49. When the head part 4 is removed, the entire device will be displaced in the direction 49 until the end surface 36 of the sleeve member 17 engages a stop detent 37.

A sleeve member or shell 38, which may be secured to the head part 4, is telescopically received on the basic body or member 10 and engages an O ring 39, which is supported on an exterior surface of the part 10. The sleeve 38 together with the head part 4 is releasably connected with the basic body member 10 by snap-in means, which are located adjacent an end surface 48 of the member 10, which surface 48 is adjacent to the head part 4. It should be noted, that the axial positioning of the head part 4 in the member 10 and thus the axial position of the drive shaft section 14 which is required for engagement of certain gear pairs is determined by the axial length of the head part which is inserted into the member 10. The snap-in means is discussed in greater detail in copending United States patent application, Ser. No. 104,980, filed Dec. 18, 1979 which was based on German application No. P 28 55 682.

As mentioned hereinbefore, the supply line 1 includes cooling lines extending to a source. These cooling lines are connected to cooling lines such as 40 in the motor part 2. The cooling lines such as 40 in the motor part 2 is connected to a cooling 41, which has an extension 41a that is connected to a cooling line 42 in the head part 4. These cooling lines enable conducting a media, such as air and water, up to a cooling spray nozzle adjacent the tool 5. To form a transfer of the media from the cooling line 40 to the cooling 41, annular channels 43 are formed on an outer surface of the member 10 and are in communication with a radial channel 44 in the bushing 11. To seal each of the channels 43, O ring seals 45 are provided so that the member 10 can be rotated relative to the bushing 11 and still convey fluid. It should be noted that in FIG. 2 only one cooling channel arrangement is illustrated although two grooves 43 are provided to enable separately conveying two fluids to the nozzle in the part.

With the head part 4 received on the handpiece part 3, a sleeve portion of the head part acts to shift the means for mounting 102 to a first position with the crown gear 23 engaged to the crown gear 25 and the gear 31 engaged with the gear 32 of the shaft 15. Since the crowns 23 and 25 have substantially the same number of teeth, the drive ratio therebetween at that connection is a 1:1 ratio. However, because the number of teeth on the gear 32 is 2½ times the number of teeth on the gear 31, the step-down ratio at that connection is 2.5:1. The RPM's applied to the shaft 15 are again step-down in the head part 4 by a ratio of approximately 1.2:1 so that a total step-down would be approximately 3:1.

When the head part 4 is removed from the basic body 10 by releasing a lock mechanism such as the above mentioned snap-in means, the entire drive shaft section 14 will be moved in the direction of arrow 49 by the compression spring 34 until an end surface 36 comes to rest against the detent 37 of the basic body portion 10. Due to this longitudinal movement, the crown gear 23 and 25 will be disengaged and the gears 27 and 24 will become engaged. When another head part, which has a drive shaft section provided with a crown gear instead of the cup-shaped gear such as 32 and has short sleeve portions to enable the means 102 to hold the section 14 in the second position, is inserted into the body 10, the crown gear of the other head part will engage the crown gear 33 to provide a direct connection with a 1:1 ratio therebetween. It should be noted, that when the gear 24 is engaged with the gear 27, that the drive shaft section 14 will be rotated at a higher speed and thus the connection between the gears 27 and 24 will produce a step up ratio of approximately 1:2.5 in the RPM transferred between sections 16 and 14.

Although various minor modifications may be suggested by those versed in the art, it should be noted that I wish to embody within the scope of the patent granted hereon, all such modifications as reasonably and properly come within the scope of my contribution to the art.

I claim:

1. In a dental handpiece having a drive motor, a grip section coupled to the drive motor and terminating in a head part having a socket for supporting a tool for rotation, said grip section having drive train means for transmitting rotational motion of the drive motor to the socket, said drive train means including at least two drive shaft sections interconnected by meshing gears, said grip section having an angle portion so that the one drive shaft section adjacent the socket extends at an angle of inclination to the other drive shaft section on the axis of the drive motor, the improvements comprising the angle of inclination being formed in at least two stages with an additional drive shaft section interposed between the one drive shaft section adjacent the socket and the other drive shaft section on the axis of the drive motor, said additional drive shaft section forming an individual angle with each of the two drive shaft sections with each individual angle being less than the angle of inclination, said grip section having a basic body portion with bores for receiving said additional drive shaft section and the other drive shaft section, and the basic body section including means for mounting the additional drive shaft section for axial displacement in one of the bores between a first and second position, said additional drive shaft section having a pair of gears disposed at each end with the gears of each pair being axially spaced apart, the other drive shaft section having a first and second gear axially spaced apart to form a pair of gears with the first gear engaging one gear of the pair of gears of the additional shaft section while the additional section is in a first position and the second gear engaging the other of said pair of gears when the additional section is in the second position, the gears of at least one of the pair of gears having different number of teeth so that a different drive ratio between the other drive shaft section and the additional drive shaft section is obtained depending on which gears are in engagement.

2. In a dental handpiece according to claim 1, wherein each of the individual angles formed by the additional drive shaft section with the two drive shaft sections is greater than one-fourth of the total angle of inclination for the handpieces.

3. In a dental handpiece according to claim 2, wherein each of the individual angles is approximately one-half the total angle of inclination.

4. In a dental handpiece according to claim 1, wherein the other drive shaft section is a component part of the drive motor.

* * * * *